(12) United States Patent
Chinnadurai et al.

(10) Patent No.: US 6,823,243 B2
(45) Date of Patent: Nov. 23, 2004

(54) OPEN-ENDED SCAN ANALYSIS WITH AUTO-IDENTIFICATION OF MULTI-PLATFORM GAS ANALYZERS

(75) Inventors: Manokar Chinnadurai, Owatonna, MN (US); Robert Kochie, Mantorville, MN (US); Douglas Mayer, Owatonna, MN (US); Phillip McGee, Owatonna, MN (US)

(73) Assignee: SPX Corporation, Charlotte, NC (US)

( * ) Notice: Subject to any disclaimer, the term of this patent is extended or adjusted under 35 U.S.C. 154(b) by 0 days.

(21) Appl. No.: 10/319,579

(22) Filed: Dec. 16, 2002

(65) Prior Publication Data

US 2004/0064227 A1 Apr. 1, 2004

Related U.S. Application Data

(60) Provisional application No. 60/413,741, filed on Sep. 27, 2000, and provisional application No. 60/413,740, filed on Sep. 27, 2000.

(51) Int. Cl.[7] .......................... G01M 15/00; G06F 17/00
(52) U.S. Cl. .............................. 701/29; 701/33; 701/35; 340/438; 340/439
(58) Field of Search .............................. 701/29, 30, 32, 701/33, 35; 340/438, 439; 709/220, 230

(56) References Cited

U.S. PATENT DOCUMENTS

| | | | | |
|---|---|---|---|---|
| 5,459,660 A | * | 10/1995 | Berra | 701/33 |
| 5,646,865 A | * | 7/1997 | Alfaro et al. | 701/29 |
| 5,884,202 A | * | 3/1999 | Arjomand | 701/29 |
| 6,128,560 A | * | 10/2000 | Ishii | 701/29 |
| 6,141,608 A | * | 10/2000 | Rother | 701/33 |
| 6,181,992 B1 | * | 1/2001 | Gurne et al. | 701/29 |
| 6,360,145 B1 | * | 3/2002 | Robinson | 701/35 |
| 2003/0004623 A1 | * | 1/2003 | Namaky et al. | 701/29 |

* cited by examiner

Primary Examiner—Michael J. Zanelli
Assistant Examiner—Eric M. Gibson
(74) Attorney, Agent, or Firm—Baker & Hostetler LLP

(57) ABSTRACT

A data display firmware improvement for a scan tool adds the capability to view in a single presentation data uploaded from a motor vehicle's onboard diagnostic (OBD) computer synchronized with data from external test apparatus. The data display algorithms permit viewing of OBD data, including certain real-time oscilloscope-like waveforms, and allow viewing test results from compatible instruments, such as exhaust gas analyzers, including capturing realtime OBD signals, holding them until delayed events such as gas analyzer test results become available, then displaying the events on a common display as though available simultaneously in real time. The present invention further permits acquisition of communication links with external test equipment for which exact protocols and port configurations may not be uniquely specified. The firmware upgrade is downloadable to existing products.

33 Claims, 7 Drawing Sheets

OPEN-ENDED SCAN ANALYSIS WITH AUTO-IDENTIFICATION OF MULTI-PLATFORM GAS ANALYZERS

RELATED APPLICATION

This application claims priority based upon Provisional Application Ser. Nos. 60/413,740 and 60/413,741, both filed Sep. 27, 2002, the disclosures of which are incorporated herein by reference.

FIELD OF THE INVENTION

The present invention relates generally to electronic test equipment. More particularly, the present invention relates to diagnostic and display apparatus for troubleshooting and repair of motor vehicles, to include interface with onboard motor vehicle control computers.

BACKGROUND OF THE INVENTION

Onboard control computers have become ubiquitous in motor vehicles, as safety, economy, and emissions requirements have continued to escalate, and conventional designs for reciprocating engines, friction braking systems, collision safety apparatus, and traction control devices have proven unequal to the requirements set out in law and the implicit demands of competitors' achievements. Successive generations of onboard control computers have acquired increasing data sensing and retention capability as the electronic art has advanced. Present external diagnostic and display apparatus, known to those skilled in the art as Scan Tools, are commonly limited to reporting the data acquired by the onboard control computer itself. Increasingly subtle subsystem failures in automobiles overload the ability of maintenance technicians not simply to read the faults detected and stored by the computers themselves, but to combine those readings with peripheral measurements in order to allow a technician to identify faults and decide on corrective actions with both speed and accuracy.

Accordingly, it is desirable to provide in the Scan Tool the ability to acquire and evaluate test data from sources other than the motor vehicle's onboard computer, and to combine those results with data acquired directly from the onboard computer. The present invention, by enhancing the Scan Tool's ability to collect data from external test devices via data input ports, and by merging the additional data with data previously available from the onboard computer into a single display with fully coordinated timing, presents to the technician a more complete picture of the status of the motor vehicle under test. By establishing communication with external test devices autonomously through a process that includes attempting and choosing among multiple protocols, the present invention speeds setup and performance of testing in a cost-driven, time-critical environment.

SUMMARY OF THE INVENTION

The foregoing limitations of the prior art have been satisfied to a great extent by the present invention, wherein, in a first aspect of the invention, a test apparatus for acquiring and displaying motor vehicle data includes a scan interface subsystem permitting communication between the test apparatus and a motor vehicle onboard diagnostic (OBD) computer, an external device interface subsystem permitting communication between the test apparatus and additional data acquisition devices, and a display in communication with the scan interface and the external device interface component, where the display presents data from the scan interface and from additional data acquisition devices with which the external device interface component may be in communication.

In accordance with another embodiment of the present invention, the Scan Tool is enhanced through the provision of means whereby vehicle status data from multiple sources can be combined and displayed. The present invention provides means whereby fixed data elements from the vehicle's OBD computer, data from the OBD computer changing at any rate, fixed measurements from other data acquisition devices, and dynamic signals from other data acquisition devices can be gathered, scaled with respect to time delay, rate, and amplitude, then stored or displayed. Whereas previous Scan Tool designs may allow OBD data, external-source data, or a combination of these to be displayed, but each test instrument must be stipulated by the user in order for its data to be captured, the present invention provides means whereby external data devices can be interrogated for their properties and their data captured and incorporated into the display without requiring the user to know their precise interface requirements.

In accordance with another embodiment of the present invention, the Scan Tool provides a method for acquiring and displaying motor vehicle diagnostic data that includes the steps of obtaining data from a computer on a motor vehicle, obtaining data from external test equipment, and displaying data from the computer on the motor vehicle and data from the external test equipment.

There have thus been outlined, rather broadly, the more important features of the invention, in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF PREFERRED EMBODIMENTS OF THE INVENTION

Figure 1:
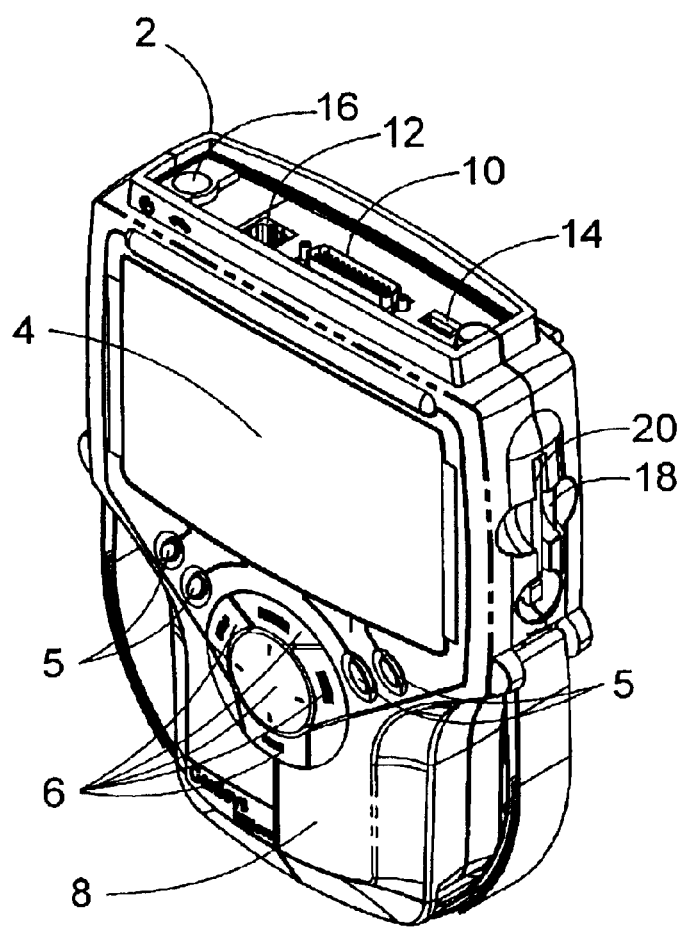
FIG. 1, an oblique front view of a hand-held Scan Tool, illustrates placement of displays, controls, and ports of a preferred embodiment of the present invention.

A preferred embodiment of the present inventive apparatus and method is illustrated in FIG. 1. In this figure, a handheld interface unit 2 has a display panel 4, a first button group 5, and a second button group 6. The shape of the preferred embodiment of the unit 2 is designed to provide large size to allow the display panel 4 to afford ease of viewing, while providing a handle 8 that allows typical users to grip the unit securely. The button group 5 in the preferred embodiment allows the bottom zone of the display to be assigned as needed as a row of up to four "soft keys" for changeable user interface options; alternative embodiments with any number of buttons and corresponding "soft keys" are possible. The button group 6 provides a set of switch closures independent of screen status, and serves as a primary user interface to the microprocessor-based Scan Tool. Ports shown in FIG. 1 are a first custom interface connector 10 for an OBD adapter, a serial port connector 12, a USB port connector 14, an Infrared Data Association (IrDA)/Hewlett-Packard (HP) Infrared connection 16, a PCMCIA type 2 connector 18 and a smart card connector 20.

Figure 2:
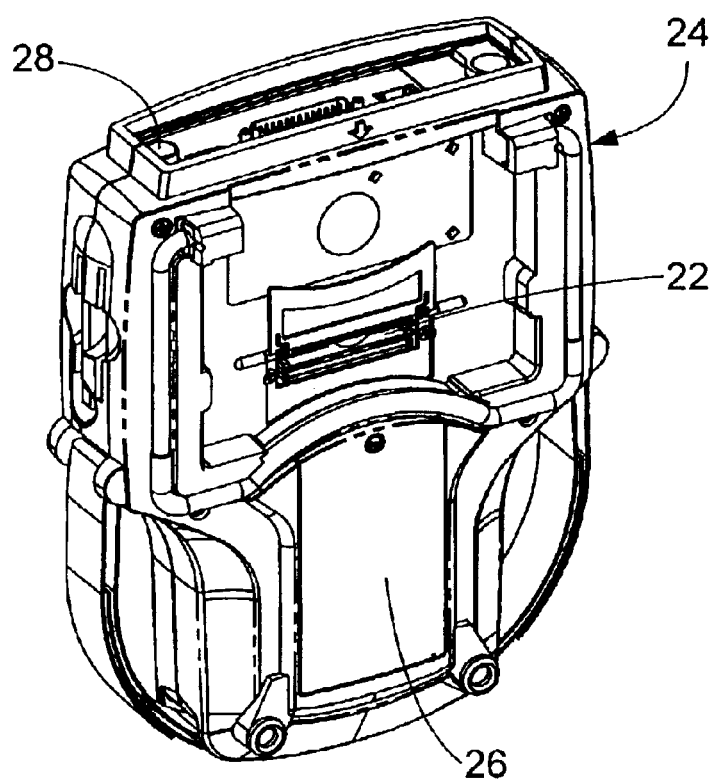
FIG. 2, an oblique rear view of the Scan Tool, illustrates connections to additional ports of a preferred embodiment of the present invention.

FIG. 2 shows the rear panel of a preferred embodiment of the invention; in this view, a second custom interface connector, termed a hardware interface port, or HIP, 22, is shown, which provides the Scan Tool with the capability of adapting functions from earlier designs to operate with the present invention. A Compact Flash® card connector 24, not visible, occupies a slot on another face of the preferred embodiment. The ports shown in the views above are representative of ports that could be included in a system design supporting the preferred embodiment of the present invention. The battery box cover 26 allows the apparatus to be powered from a built-in Nickel-Metal Hydride (NiMH) battery. The preferred design permits a power supply that can furnish the requisite direct-current (DC) voltage at sufficient amperage to be plugged into a power jack 28, supporting in-unit recharging of the NiMH battery and allowing indefinite operating time.

Figure 3:
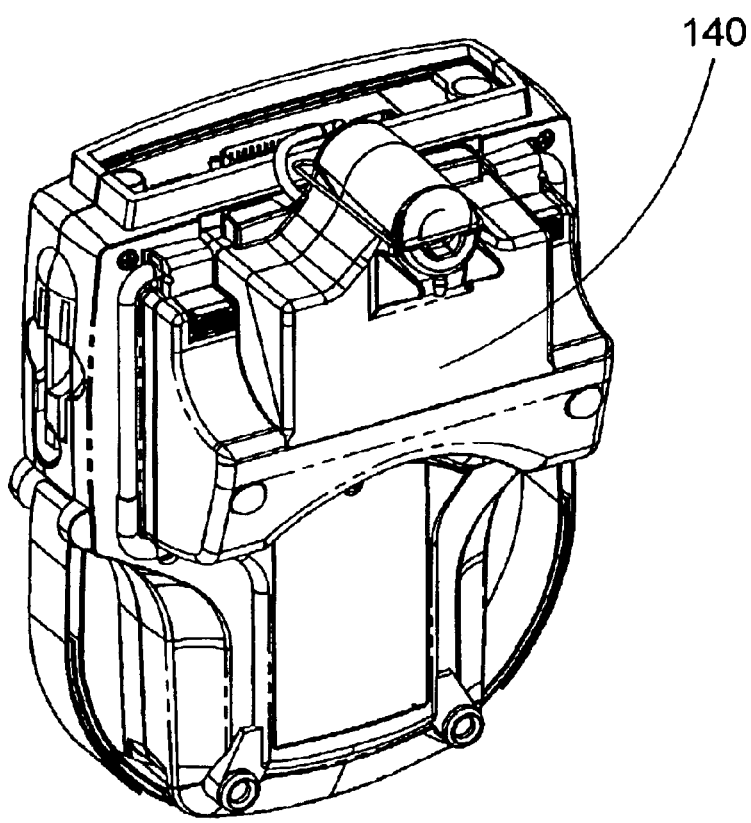
FIG. 3, a view similar to FIG. 2, shows the Scan Tool with a representative Gas Analyzer fitted into a recess in its rear surface and mated to the connector therein.

FIG. 3 shows the view of FIG. 2 with a typical Gas Analyzer 140 installed. Such a Gas Analyzer, directly mating with the HIP connector 22, may carry one of a variety of communications interfaces with which the inventive apparatus is compatible. Other Gas Analyzer modules that can function with the preferred embodiment may communicate with it through alternative ports, such as the serial port 12, and may use other protocols than that used by the Gas Analyzer 140.

Figure 4:
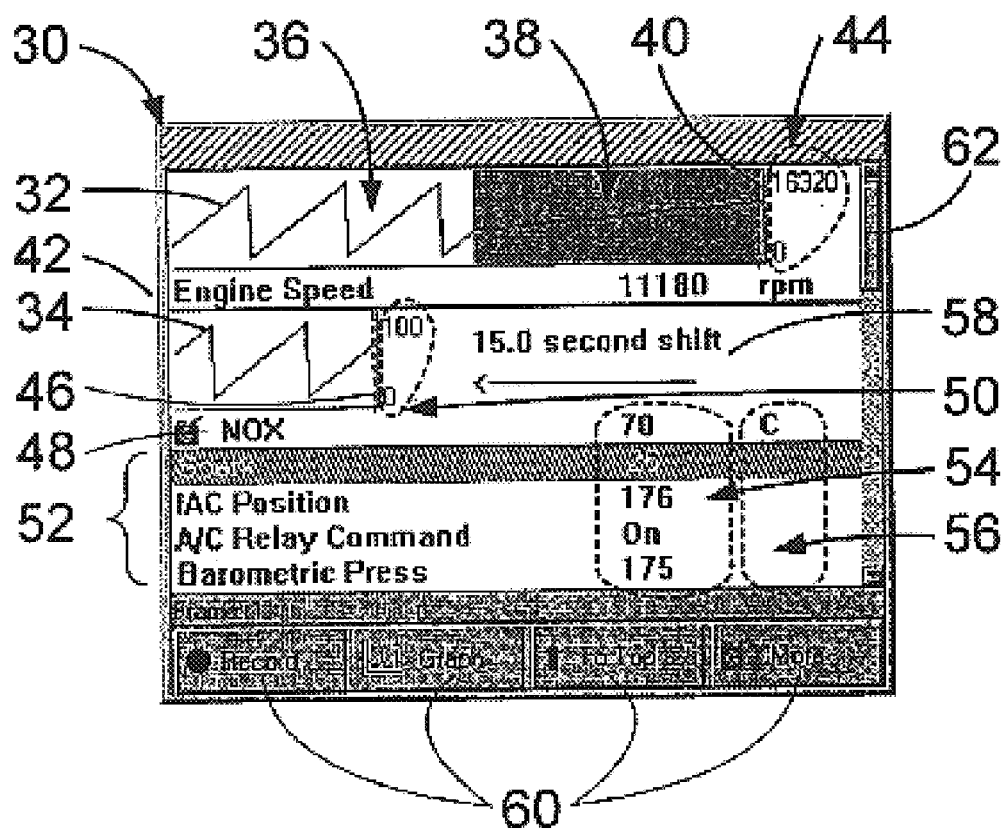
FIG. 4 provides a representative view of the Scan Tool's display, in which typical data items are presented and soft keys are shown, available for user activation.

FIG. 4 illustrates the display of one embodiment, wherein a full-color display screen 30 has facility to present a plurality of time (horizontal axis) versus selected parameter (vertical axis) data events, as well as text information. The capability of the concept is illustrated by a first trace 32 that shows engine revolutions per minute (RPM) as a function of time during a particular test session, and a second trace 34 that shows exhaust gas concentration of oxides of nitrogen, the latter data having been acquired at a different time during the same test interval. The horizontal axis of the display shows a low-resolution section 36 and a high-resolution section 38, which capability is a selectable function of the preferred embodiment. A first dashed line 40 indicates the exact point on the time axis that corresponds to a first text readout 42, which provides a descriptive label, a value, and a unit reference; a first pair of minimum and maximum readings 44 is provided to establish a scale. The second trace 34 represents data from an external test device, which data is available after a fixed delay. The display is offset accordingly, allowing the two readings to be aligned in time. A second dashed line 46 indicates the sample time for a second text display 48. A second scale indication 50 provides a second frame of reference.

The display shows a plurality of additional test items in the form of text only, which can include labels 52, data values 54, and units 56 where relevant. The display further shows representative status information, such as a note 58 indicating the delay time for the gas sensor. A group of "soft" buttons 60 have functions dynamically defined, with activation for the immediate definitions of the button functions triggered through the buttons shown in FIG. 1 as item 6. A slidebar 62, familiar to users of graphical user interface (GUI)-based operating systems such as Lynx®, Apple® OS9®, and Microsoft® Windows®, indicates the presence of and provides access to additional data not presently visible on the display.

Figure 5:
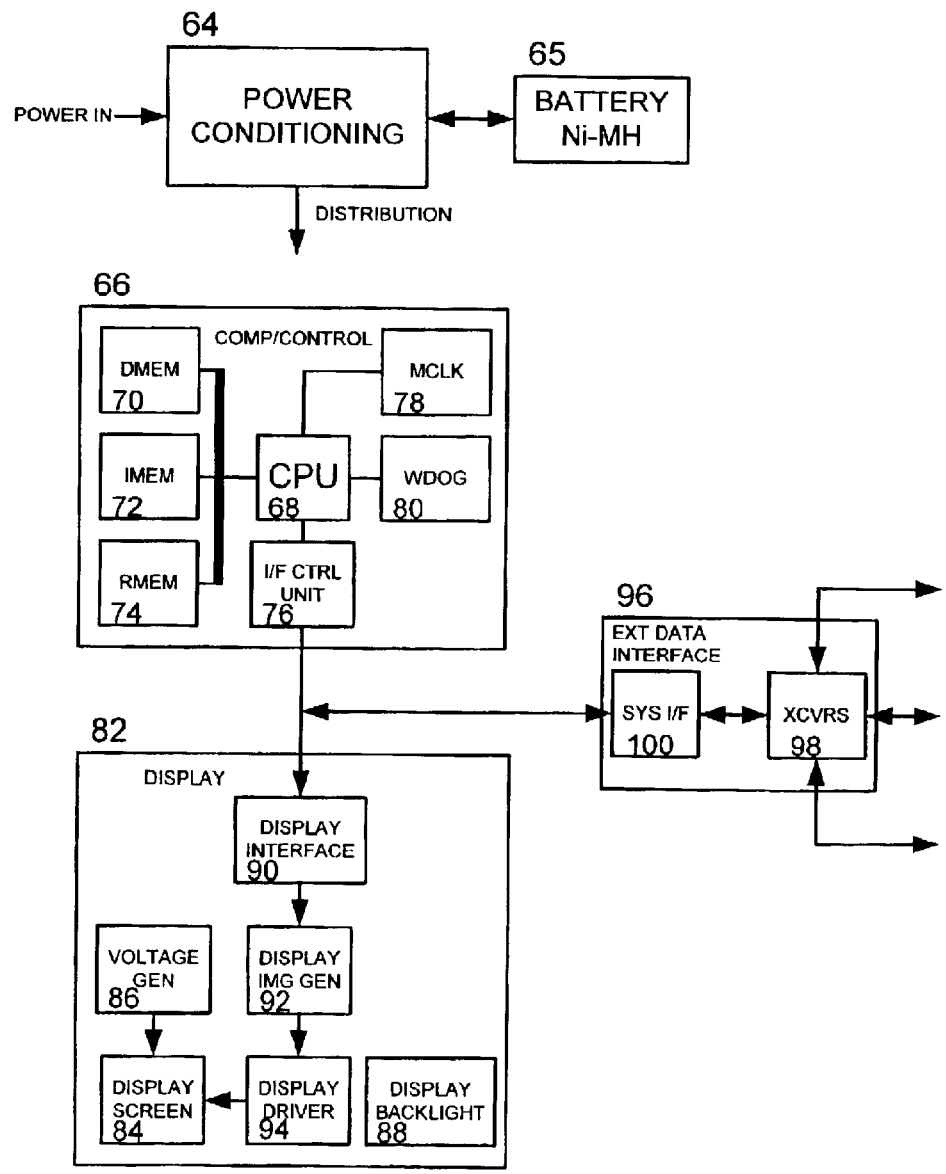
FIG. 5 is a block diagram showing the functional units of the present invention.

FIG. 5 illustrates the electronic circuitry in block diagram form. A power-input subsystem 64 accepts available DC and converts it to the voltages needed for all other subsystems within the apparatus. A computational subsystem 66 that includes a central processing unit 68, a dynamic data memory area 70, a preprogrammed instruction memory area 72, a reprogrammable instruction and data area 74, an interface control unit 76, a master clock 78, and a watchdog timer 80, performs analysis and control of all functions. A display subsystem 82 that includes a display screen 84, a dedicated display voltage generator 86, a backlight voltage generator 88, a display interface unit 90, a display image generator 92, and a display driver 94, accepts, stores, and displays data generated by the computational subsystem 66. An external data interface unit 96 that includes a set of transceivers 98 and a dedicated data interface processor 100 receives digital data from installed external test instruments requiring such dedicated handshaking and presents this data to the computational subsystem 66, which collates and processes that data. The external data interface unit 96 further transmits such digital handshaking and control data as the external test instruments may require in order to continue providing measurements.

Figure 6:
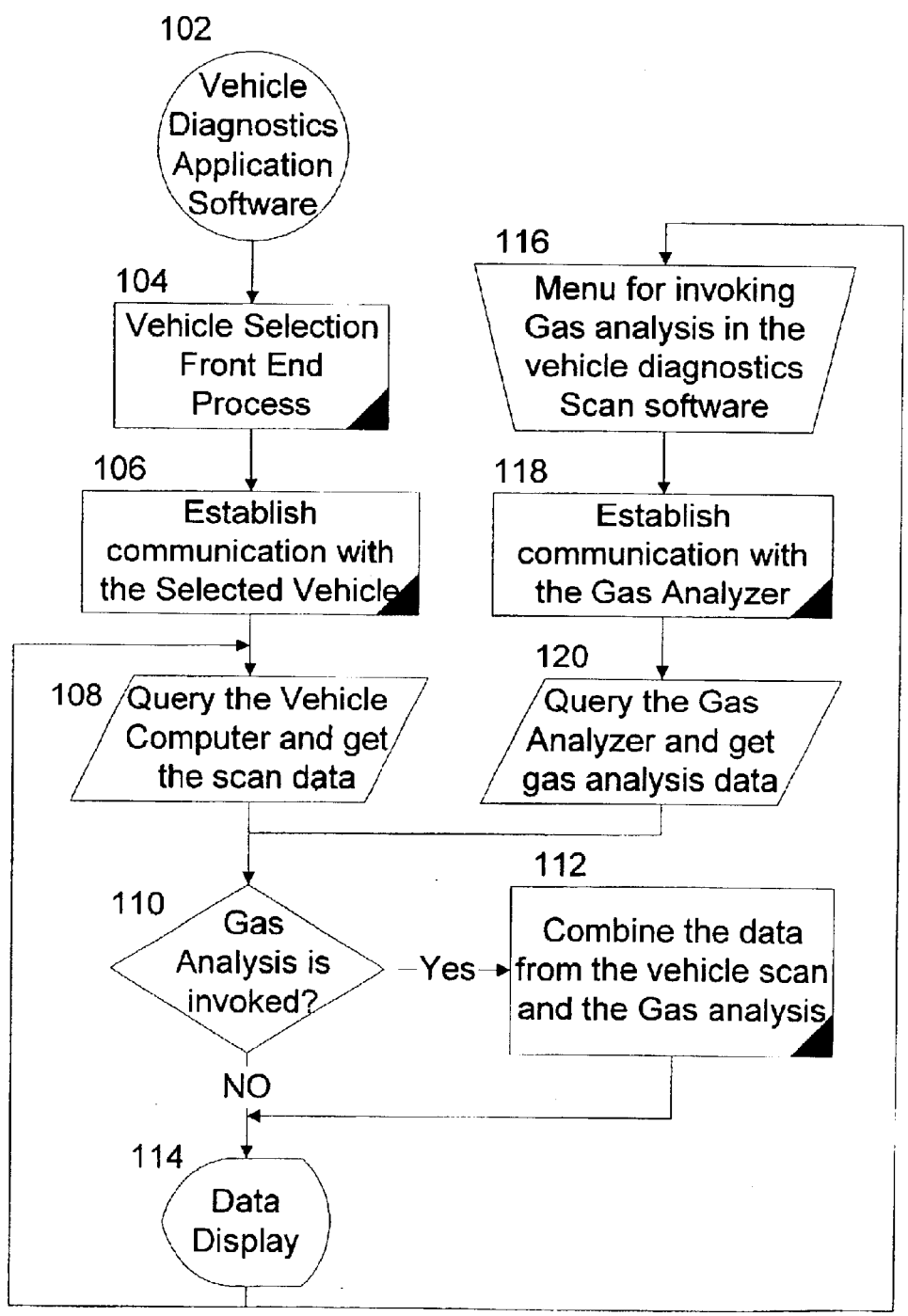
FIG. 6 and FIG. 7 are summarized flowcharts illustrating the steps that may be followed in performance of the functions of the present invention, including and identifying new functions embodied in the present invention.

FIG. 6 shows one of the major elements included in the present invention. In this flowchart, operation begins with basic initialization 102. The call to the Vehicle Selection Front End Process 104 (VS Process) identifies the vehicle under test through a process combining user interface and data table lookup.

In one embodiment, VS Process 104 software will guide an operator through interpretation of the characters of the VIN, such as an "F" in the second position indicating a Ford or a "G" in the tenth position representing the year 1986. For each of several combinations of position and data value, the VS Process 104 permits the operator to compile a description of the vehicle under test.

In another embodiment, the operator can key in a vehicle identification number (VIN) and the Scan Tool can determine the manufacturer, body style, year of manufacture, engine type, emissions controls, settings that can be stored and changed in OBD memory (spark advance timing and the like), and other details concerning that vehicle, all of which may be stored in the Scan Tool in the reprogrammable instruction and data area 74.

Some of the data acquired through any embodiment of the VS Process 104 is needed in running the diagnostics; other information, such as the part of the VIN that is the serial number of the particular vehicle, is stored for printing, added to a database where the service is performed, or otherwise used.

Once the vehicle has been selected, communication between the Scan Tool and the vehicle must be established 106. Since several vehicle manufacturers use OBD specification compliant interfaces that are not compatible with each other, the process in 106 requires a dedicated interface driver and cable set as well as a unique handshaking routine. A representative Scan Tool can manage this process by directing the operator to assemble the system in the configuration required for the particular vehicle. This process is complete when the Scan Tool is able to verify that the test system components are correctly connected and has performed handshaking with the vehicle's OBD electronics. For vehicles older than the industry's adoption of the OBD system, other interconnect systems can be used.

Once communication is established 106, the Scan Tool can extract 108 from the OBD of the vehicle under test any static scan data of interest. As part of this process, the Scan Tool may also determine criteria for extracting from the OBD any data that may flow in real time and be susceptible to capture by the Scan Tool in support of its testing. The first trace 32 in FIG. 4 is such a realtime flow, captured and stored for subsequent display. Such a data flow could also be displayed in real time and not captured, in much the same way that a vehicle scope could monitor a spark plug waveform, for example.

FIG. 6 includes a specific query 110 related to Gas Analyzers. While other external devices may be treated similarly, the management of Gas Analyzers in particular is an illustrative example of the data management that is the subject of the present invention. If no Gas Analyzer is needed (the NO branch at the decision point 110), then the logic shown displays by default all acquired and selected data in a single time frame 114. There are exceptions to this. The inventive design allows data that arrive at the same time to be displayed offset in time; the same data stream to be displayed more than once on separate lines, at the same time or skewed in time; or data streams to be held indefinitely, displayed later, printed, transmitted to an external device; and so on. Note that there is a loop from the Data Display 114 that feeds back before the vehicle query 108. This loop represents the continuous data acquisition that a representative Scan Tool performs.

If inclusion of Gas Analyzer data was selected by the user, then another feature of the inventive apparatus comes into play, because a multiplicity of Gas Analyzers, some with incompatible communications interfaces, are in current use. In the case where use of a Gas Analyzer as part of an analysis was previously selected, then an additional step in the process combines 112 the Gas Analyzer data with the remainder of the Scan Tool data according to the user's preferred format. Where the Gas Analyzer was chosen but has not yet been started, the secondary loop path from Data Display, which is normally inactive, responds to a manual input 116—in this case, the manual input consists of scrolling to the desired setup window on the display and pressing the button corresponding to the desired option—by launching the setup routine. This begins by establishing communication with whichever Gas Analyzer is connected 118 as described in the narrative for FIG. 7 below. Next, the data link to the Gas Analyzer is exercised according to the requirements of the unit that is installed, and flow of gas data is begun 120. At this point data flow and Scan Tool operation substantially merge with those of the default path described first, namely continuous reacquisition of all available fixed and dynamic data from all sources, then displaying a subset of it in accordance with user-selected options.

Figure 7:
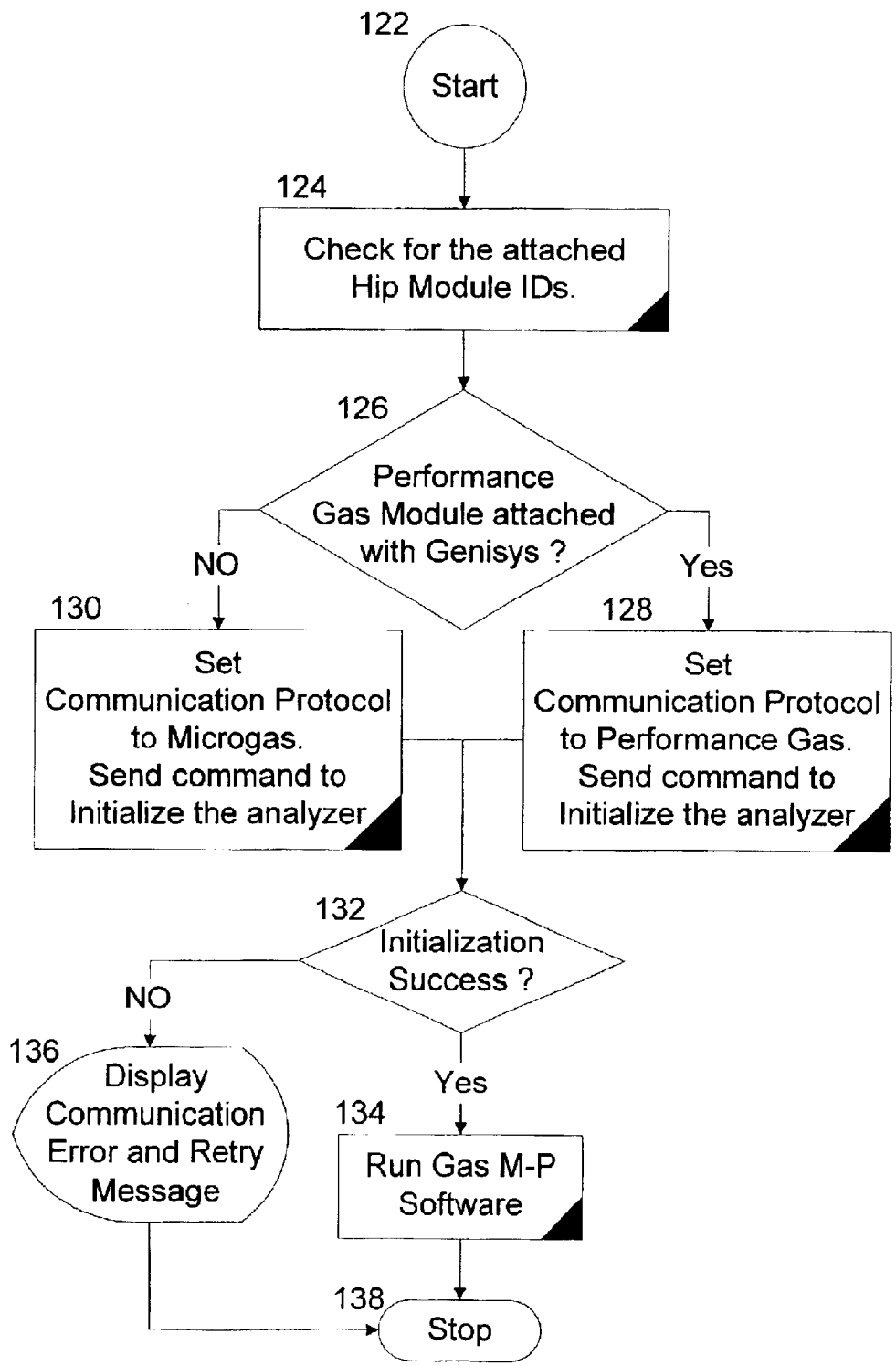

In flowchart FIG. 7, initialization of a Gas Analyzer by the inventive apparatus is summarized. This flowchart assumes successful initialization of other elements of the Scan Tool programming, picking up the initialization process where the multiple Gas Analyzer management capability of the present invention is applied. Here, at the Start node 122, Scan Tool initialization invokes the new routine. The first result of choosing to use the Gas Analyzer is that the software strobes the HIP connector 22, as step 124. If any compatible device is attached, it will respond with its code number. Inquiry 126 of a configuration lookup table will determine whether the code number of that installed device is assigned to a Gas Analyzer. If it is, then the Scan Tool can command initialization 128, which both sets up the communications link to the Gas Analyzer and causes the Gas Analyzer to begin its startup and run sequence.

If the inquiry 126 result does returns negative, in this instance meaning that the Scan Tool's HIP connector does not carry a Gas Analyzer, then the software next assumes that a serial-port connected Gas Analyzer, termed in the flowchart a "Microgas®", is expected, and the Scan Tool transmits serial handshake and initialization signals 130. Any number of handshake routines unique to different external test devices may be transmitted on any number of the Scan Tool's ports, so long as the protocols and configurations of candidate devices are well enough defined to permit a successful identification and activation of a device.

At the end of whichever predefined initialization sequence was required, the Scan Tool evaluates 132 the initialization results. If the initialization routine completed successfully, confirming the installation and good operating condition of the chosen device, then the loop falls through to allow the user to configure the display to incorporate the Gas Analyzer test results and execute Gas Analyzer software 134.

If the expected results do not return from the initialization sequence, then a fault beyond the limits of software, such as failure to actually connect the device or a fault in the device itself, has occurred, and the software places a message on the Scan Tool display 136, which is the end of the routine 138. Other than this fault message, the Scan Tool continues to operate its other normal functions.

The system configuration here refers to accessory devices attached to the main unit and active during the current session. Some devices may be unused, others may be self-configuring, others still may require manual setup by the user. Among devices nominally self-configuring, some may permit manual intervention. As an example, the time lag for a particular model of Gas Analyzer might be known and calibrated, but a technician might wish to alter the apparent time lag. Similarly, the nominal time lag could be subject to drift and require compensation. Such manual configuration changes could be made at this point in the logic flow.

Normal execution involves time-shared execution of all scheduled tasks. Time-slice allocation is a task carried out by the operating system. The scheduled tasks are managed as objects with hierarchical priority. Interrupts are controlled in such fashion as to avoid system and task casualties.

One embodiment of the present invention can provide additional digital data input management capability and a revised command package for an existing Scan Tool design. The additional input capability can take the form of management of port connections to permit multiple external devices to provide test results that can be displayed by the Scan Tool. The revised command package can format and store test data from external test equipment as well as data captured by the vehicle's OBD computer and uplinked. The command package can further coordinate display of selectable subsets of the stored data from all sources. Data arriving from stored sources may typically be unchanging over the course of a test. Realtime data from onboard and external sources may detect discrete events that occurred at different rates. Continuous processes may have been sampled at different rates. As a consequence of these factors, it can be a requirement of the command package to coordinate and rationalize data from all sources in order to display disparate information on a common timeline. This coordination and rationalization can take the form of storing time versus data for each changeable item; storing values for items that are intrinsically invariant over the course of a test; and storing correction factors such as gain, characteristic or programmable time delay.

In accordance with one embodiment of the present invention, the Scan Tool has the following new capabilities:

It can extract and store in its own memory all entries specified for an OBD-II-compliant computer's storage, including indications of both normal and abnormal conditions, time or event count information, and such other data as a particular OBD computer may store.

It can acquire from external sources and retain any compatibly formatted data furnished by additional test instruments monitoring the motor vehicle under test.

It can present to the display subsystem of the Scan Tool a combined test result, composed of static (fixed or rarely changing) and dynamic (changing frequently or continuously) reports from the OBD computer of the vehicle under test, as well as static and dynamic reports from external test instruments.

It can furnish test results to the display subsystem of the Scan Tool selectively from all those available, at the choice of the user.

It can allow control over the timing relationship between displays of individual events, so that any display may be delayed with respect to a timing reference.

It can allow control over the time interval for the combined display, so that the display presents events that occurred over a time segment that the user can select.

It can provide both compressed and expanded time intervals for the displayed events, so that the time axis can be in part "zoomed out" to permit display of large amounts of data at low time resolution and "zoomed in" to permit display of smaller amounts of data at higher time resolution.

It can provide control of the time window for the combined display, so that any time segment within the capability of the hardware implementation may be displayed, and the user may pass the display back and forth repeatedly through the stored data, displaying any such data of interest.

It can permit input management parameter entry for characterization of source signals, including but not limited to telemetry voltage excursion, telemetry signal timing and format, digital signal numerical range, data acquisition time lag, signal labeling, and units labeling.

It can identify and acquire communications synchronization with an unknown external instrument attached to a port through a process of transmitting multiple initialization protocols on multiple ports and monitoring reply lines for appropriate responses, thereby allowing a user to add an unfamiliar instrument to a test setup and use it successfully without explicit knowledge of its parameters.

The many features and advantages of the invention are apparent from the detailed specification, and thus it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A test instrument for acquiring and displaying motor vehicle data, comprising:

a scan interface component permitting communication between said test instrument and a motor vehicle onboard diagnostic (OBD) computer;

an external device interface component permitting communication between said test instrument and an additional data acquisition device; and a communication subsystem configured to scan the external device interface to determine a connection of said additional data acquisition device and in response to the determination of the connection of the additional data acquisition device, the communication subsystem attempts to establish a communications connection between said test instrument and said additional data acquisition device.

2. The test instrument of claim 1, further comprising additional external device interface component permitting communication between said test instrument and a plurality of additional data acquisition devices.

3. The test instrument of claim 1, further comprising a subsystem of said test instrument to display test and status data in graphical form, to include text messages.

4. The test instrument of claim 1, further comprising a subsystem of said test instrument to display test and status data in graphical form, to include representation of a horizontal axis representing time plotted against a vertical axis representing a test parameter, selected from the group consisting of voltage, temperature, concentration of oxides of nitrogen, and other parameters of interest to test instrument users.

5. The test instrument of claim 1, further comprising a subsystem of said test instrument able to alter graphical display representation of data collected from said vehicle OBD computer in response to data properties of event time of occurrence, data item acquisition rate, and amplitude, for the purpose of permitting comparison between said data despite disparities in properties.

6. The test instrument of claim 1, further comprising a subsystem of said test instrument able to alter graphical display representation of data collected from said additional data acquisition device in response to disparate data properties of event time of occurrence, acquisition device data acquisition rate, and amplitude, for the purpose of permitting direct data comparison despite disparities in event rate.

7. The test instrument of claim 1, further comprising a subsystem of said test instrument able to alter graphical display representation of data collected from said additional data acquisition device in response to disparate data properties of event time of occurrence, acquisition device data acquisition rate, and amplitude, for the purpose of permitting direct data comparison despite disparities in time of occurrence.

8. The test instrument of claim 1, further comprising a subsystem of said test instrument able to alter graphical display representation of data for the purpose of permitting the horizontal axis of a time-synchronized set of data traces to display in part at a first rate and in part at a second rate.

9. The test instrument of claim 1, further comprising a subsystem of said test instrument able to display data previously acquired.

10. The test instrument of claim 1, further comprising a subsystem of said test instrument able to alter a time representation of sets of data in order to display the sets of data that occurred at different times.

11. The test instrument of claim 1, further comprising a system of said test instrument able to acquire and process data from a motor vehicle onboard diagnostic type II (OBD-II) computer scan interface using universal OBD-II interface ports and protocols.

12. The test instrument of claim 1, further comprising a system of said test instrument configured to write data to a motor vehicle onboard computer using universal OBD-II interface ports and protocols.

13. The test instrument of claim 1, further comprising a subsystem of said test instrument able to acquire and process data from, output commands and data to, said additional data acquisition device, where said additional data acquisition device employs an interface port and protocol to supply data.

14. The test instrument of claim 1, further comprising a subsystem of said test instrument able to acquire and process data from said additional data acquisition device, where such said additional data acquisition device employs an industry-standard Infrared Data Association® (IrDA) infrared interface port and protocol to communicate.

15. The test instrument of claim 1, further comprising subsystem of said test instrument configured to acquire and process data from, output commands and data to, external test apparatus, where such said additional data acquisition device employs an industry-standard serial interface port and protocol to communicate.

16. The test instrument of claim 1, further comprising an interface of said test instrument able to acquire and process data from, output commands and data to, said additional data acquisition device, where such interface employs an industry-standard Personal Computer Memory Card International Association® (OCNCIA®) interface port and protocol to communicate.

17. The test instrument of claim 1, further comprising a subsystem of said test instrument able to acquire and process data from, output commands and data to, said additional data acquisition device, where such said additional data acquisition device employs an industry-standard universal serial bus (USB) interface port and protocol to supply data.

18. The test instrument of claim 1, further comprising a subsystem of said test instrument configured to output data to said additional data acquisition device, where said additional data acquisition device employs a Hewlett-Packard Corporation® (HP®) wireless interface port and protocol to output data.

19. The test instrument of claim 1, further comprising a subsystem of said test instrument able to acquire replacement executable binary code for said test instrument from an external source, where said additional data acquisition device employs an industry-standard Class II Compact Flash Card® interface port and protocol to supply replacement executable binary code.

20. The test instrument of claim 1, further comprising a subsystem of said test instrument able to acquire replacement executable binary code for said test instrument from said additional data acquisition device, where said additional data acquisition device employs an industry-standard universal serial bus (USB) interface port and protocol to supply replacement executable binary code.

21. The test instrument of claim 1, further comprising a subsystem of said test instrument able to establish communication with said additional data acquisition device, where said additional data acquisition device employs an interface and protocol not explicitly specified prior to the initialization of communication, said communication being established by the test instrument transmitting multiple handshaking sequences and monitoring multiple possible response lines until a successful link is established.

22. The test instrument of claim 1, further comprising a subsystem of said test instrument able to establish communication with said additional data acquisition device, where said additional data acquisition device employs an interface and protocol not explicitly specified prior to the initialization of communication, said communication being established by the test instrument by transmitting multiple handshaking sequences using possible control nodes and monitoring available response nodes until all sequences available to said test instrument have been exhausted, after which the most successful protocol for that external test apparatus is reinvoked.

23. A system for acquiring and displaying motor vehicle diagnostic data, said system comprising:
   means for acquiring data generated or stored within a motor vehicle computer;
   means for communicating with an external test instrument;
   means for scanning the means for communicating to determine the connection of said external test instrument;
   means for establishing a communication connection with said external test instrument through repeated attempts to initialize a communication link with said external test equipment using differing protocols and port configurations; and
   means for acquiring data from said external test instrument.

24. The system of claim 23, further comprising means for processing data acquired from said motor vehicle computer and said external test instrument.

25. The system of claim 23, further comprising means for altering data stored within said motor vehicle computer.

26. The system of claim 23, further comprising means for transmitting commands for execution by said external test instrument.

27. The system of claim 23, further comprising means for displaying data from said motor vehicle computer and said external test instrument in a unified graphical display.

28. A method for acquiring and displaying motor vehicle diagnostic data comprising the steps of:
   obtaining data from a computer within a motor vehicle through a link to a scan tool;
   scanning a communications port of the scan tool to determine a connection of an external test instrument;
   in response the determination of the connection, establishing a communications connection between the scan tool and the external test instrument; and
   obtaining data from the external test instrument.

29. The method of claim 28, further comprising the step of displaying selected data signals in accordance with selected settings, independent of the source of the signals.

30. The method of claim 28, further comprising the step of processing data signals.

31. The method of claim 28, further comprising the step of altering data stored within the computer on the motor vehicle.

32. The method of claim 28, further comprising the step of transmitting commands for execution by external test equipment.

33. The method of claim 28, further comprising the step of displaying data from the computer on the motor vehicle and external test instrument in a unified graphical display.

* * * * *